(12) United States Patent
Martin et al.

(10) Patent No.: US 10,548,581 B2
(45) Date of Patent: Feb. 4, 2020

(54) SURGICAL SHIELD

(71) Applicant: Ossis Limited, Christchurch (NZ)

(72) Inventors: Madeleine Bess Martin, Christchurch (NZ); Malcolm Keith Gordon, Christchurch (NZ); Timothy John Dunn, Christchurch (NZ)

(73) Assignee: Ossis Limited, Christchurch (NZ)

(*) Notice: Subject to any disclaimer, the term of this patent is extended or adjusted under 35 U.S.C. 154(b) by 601 days.

(21) Appl. No.: 15/301,918

(22) PCT Filed: Apr. 2, 2015

(86) PCT No.: PCT/NZ2015/050041
§ 371 (c)(1),
(2) Date: Oct. 4, 2016

(87) PCT Pub. No.: WO2015/152738
PCT Pub. Date: Oct. 8, 2015

(65) Prior Publication Data
US 2017/0112482 A1 Apr. 27, 2017

(30) Foreign Application Priority Data

Apr. 4, 2014 (NZ) .................................. 623466
Aug. 21, 2014 (NZ) .................................. 629138

(51) Int. Cl.
*A61B 46/00* (2016.01)
*A61B 17/02* (2006.01)
*A61B 17/00* (2006.01)
*A61B 90/00* (2016.01)

(52) U.S. Cl.
CPC .............. *A61B 17/02* (2013.01); *A61B 46/00* (2016.02); *A61B 2017/00778* (2013.01); *A61B 2017/0262* (2013.01); *A61B 2090/08021* (2016.02)

(58) Field of Classification Search
CPC . A61F 2/06; A61L 27/18; A61B 90/00; A61B 2090/0815; A61B 2090/0816; A61B 46/10; A61B 17/02; A61B 46/30; C08L 83/04
See application file for complete search history.

(56) References Cited

U.S. PATENT DOCUMENTS 3,577,837 A    5/1971   Bader, Jr.
3,823,705 A *  7/1974   Trimble .................... A61F 2/06
                                                    600/37
4,013,078 A    3/1977   Feild
(Continued)

OTHER PUBLICATIONS

International Preliminary Report on Patentability prepared by the Australian Patent Office in connection with PCT/NZ2015/050041, dated Aug. 11, 2015.
(Continued)

*Primary Examiner* — Ophelia A Hawthorne
(74) *Attorney, Agent, or Firm* — Richards Patent Law P.C.

(57) ABSTRACT

The invention relates to a surgical shield, wherein the shield includes one or more walls including at least one substantially smooth surface, the one or more walls individually or collectively forming a single substantially elongate member; and at least one attachment means directly or indirectly attached to the one or more walls for securing the shield in position during a surgery.

24 Claims, 7 Drawing Sheets

(56) References Cited

U.S. PATENT DOCUMENTS

| | | | |
|---|---|---|---|
| 4,889,107 A * | 12/1989 | Kaufman | A61B 17/02 |
| | | | 600/206 |
| 5,395,354 A | 3/1995 | Vancaillie | |
| 5,868,745 A | 2/1999 | Alleyne | |
| 7,112,221 B2 | 9/2006 | Harris | |
| 9,333,069 B2 * | 5/2016 | Denham | A61B 17/0401 |
| 2012/0136401 A1 | 5/2012 | Shelokov | |
| 2012/0203069 A1 | 8/2012 | Hannaford et al. | |

OTHER PUBLICATIONS

International Search Report prepared by the Australian Patent Office in connection with PCT/NZ2015/050041, dated Jul. 15, 2015.
Written Opinion of the International Searching Authority prepared by the Australian Patent Office in connection with PCT/NZ2015/050041, dated Jul. 1, 2015.

* cited by examiner

SURGICAL SHIELD

FIELD OF INVENTION

The present invention relates to a shield for temporarily repositioning a blood vessel and/or protecting a body part, such as a blood vessel, lymphatic vessel or ureter, during surgery.

BACKGROUND TO THE INVENTION

At present, blood vessels usually are temporarily repositioned during surgery by exposing them, moving them to the desired new position, and holding them in that position using one or more small pins, one end of the or each pin being inserted into any suitable adjacent bone.

However, this practice has the drawback of curving the blood vessel around a small diameter pin and this can lead to an unacceptably high pressure on the wall of the blood vessel in contact with the pin, and even to kinking of the blood vessel; both of these events have the potential to damage the blood vessel.

A further drawback is that the relatively small diameter of the pin may allow the blood vessel to curve back into the area from which it needs to be temporarily removed for surgical purposes; this also risks damage to the blood vessel.

In the case of an anterior spinal fusion procedure, the iliac veins generally need to be temporarily repositioned during the spinal fusion procedure to fuse the L 4 and L 5 (or the L 5/S 1) vertebrae. Damage to the iliac veins can lead to a massive haemorrhage and it is therefore very important that the veins are both protected and temporarily repositioned during surgery, without any risk of damage to the veins.

A further potential problem is that anatomy is not standard from person to person, and can vary widely. It is therefore important that any device or technique for temporarily repositioning a blood vessel can be varied easily and rapidly, as necessary to suit different anatomies.

OBJECT OF THE INVENTION

It is an object of the present invention to provide a shield for protecting and temporarily repositioning a blood vessel during surgical procedures which overcomes the above described the problems.

Alternatively, it is an object of the invention to at least provide the public with a useful choice.

SUMMARY OF THE INVENTION

Preferred aspects of the invention are set forth in the appended claims. Particular embodiments are described below in non-limiting terms.

According to a first embodiment of the invention there is provided a surgical shield, wherein the shield includes one or more walls including at least one substantially smooth surface, the one or more walls individually or collectively forming at least one substantially elongate member; and at least one attachment means directly or indirectly attached to the one or more walls for securing the shield in position during a surgery.

In preferred embodiments of the invention, the one or more walls is a single elongate strip of flexible material.

In further preferred embodiments, the elongate strip is curved in at least one direction.

More preferably, the elongate strip is curved across the at least a portion of the width of the elongate strip or along at least a portion of the length of the elongate strip.

Preferably, the shield is formed from a flexible material.

More preferably, the flexible material is capable of plastic or elastic deformation.

In alternative embodiments, the shield includes one or more curvature support means to enable the shield to be bent into and retained in various positions.

In one embodiment the one or more curvature support means may be in the form of one or more wires or wire lattices located within the one or more walls.

In further preferred embodiments the surgical shield includes a taper along the length one or both side edges of the elongate member such that a first end of the elongate member has a greater width than the second end of the elongate member.

In alternative embodiments one or both of the side edges of the elongate member includes a notch, cut out portion or irregular edge to correspond to a specific anatomical region.

In further preferred embodiments, the surgical shield includes an elongate strip of smooth, resilient, material providing along its length a smooth, gradual curve through an obtuse angle, such that the walls of the elongate strip include a first smooth surface providing a convex curve, said a convexly curved surface of said shield also providing a concave curve across its width; and one or more attachment means.

In preferred embodiments, the attachment means is in the form of an aperture, groove, pin, screw, hook, nail or clip.

In further preferred embodiments, the attachment means is an aperture adapted to receive a pin.

In alternative embodiments, the attachments means is an over-moulded pin.

Preferably, the shield and attachment means are integrally formed.

In alternative embodiments the surgical shield includes at least one means for releasably connecting to a second surgical shield.

Preferably, the means for releasably connecting two or more surgical shields is selected from a friction fit mechanism, clip-fit mechanism, lock and key mechanism, hook, rim, pin or screw.

In further preferred embodiments the shield of the present invention is manufactured using injection moulding, additive manufacturing or using plastic machining techniques.

According to a second embodiment of the invention there is provided a method for shielding soft tissue during a surgical process, the method including the steps of;
  a) positioning a protective guard, shield or barrier at a specific location within a patient body, the guard, shield or barrier positioned substantially between the soft tissue to be protected and a surgical site;
  b) securing the shield, guard or barrier to surrounding tissue or bone using an attachment means.

In preferred embodiments, the method includes shielding a blood or lymphatic vessel during a surgical process.

In further preferred embodiments, the method includes the use of a surgical shield as described in more detail above.

According to a third embodiment of the invention there is provided a method for repositioning a blood vessel, lymphatic vessel, nerve or ureter during a surgical procedure, the method including the steps of;
  a) exposing a blood vessel, lymphatic vessel, nerve or ureter within a patient's body;

b) positioning the blood vessel, lymphatic vessel, nerve or ureter within the curve of a surgical shield as described above;

c) moving the shield away from the original location to a second removed position; and d) attaching the shield in the removed position to the patient using the attachment means.

Further aspects of the invention, which should be considered in all its novel aspects, will become apparent to those skilled in the art upon reading of the following description which provides at least one example of a practical application of the invention.

DESCRIPTION OF THE DRAWINGS

One or more embodiments of the invention will be described below by way of example only, and without intending to be limiting, with reference to the following drawings, in which.

DETAILED DESCRIPTION OF PREFERRED EMBODIMENTS OF THE INVENTION

The shield of the present invention may be used for supporting and protecting the iliac vein while performing an anterior spinal fusion procedure, and will be described with particular reference to this application. However, it will be appreciated that the shield of the present invention would also be useful for temporarily repositioning and/or protecting body parts during any of a wide range of procedures.

Figure 1:
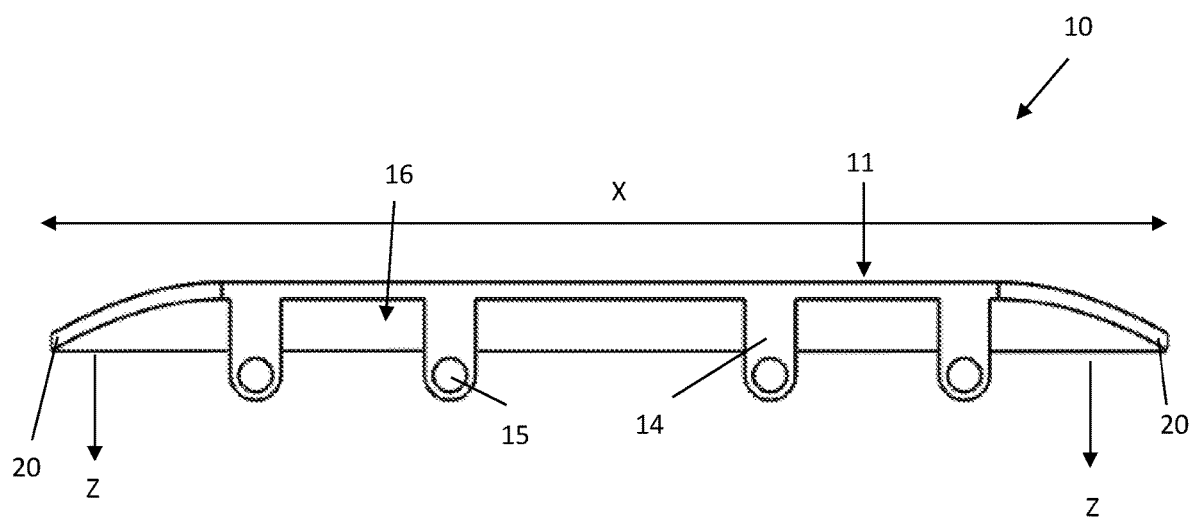
FIG. 1 shows a side view of a blood or lymphatic vessel shield in accordance with one embodiment of the present invention.
Figure 2:
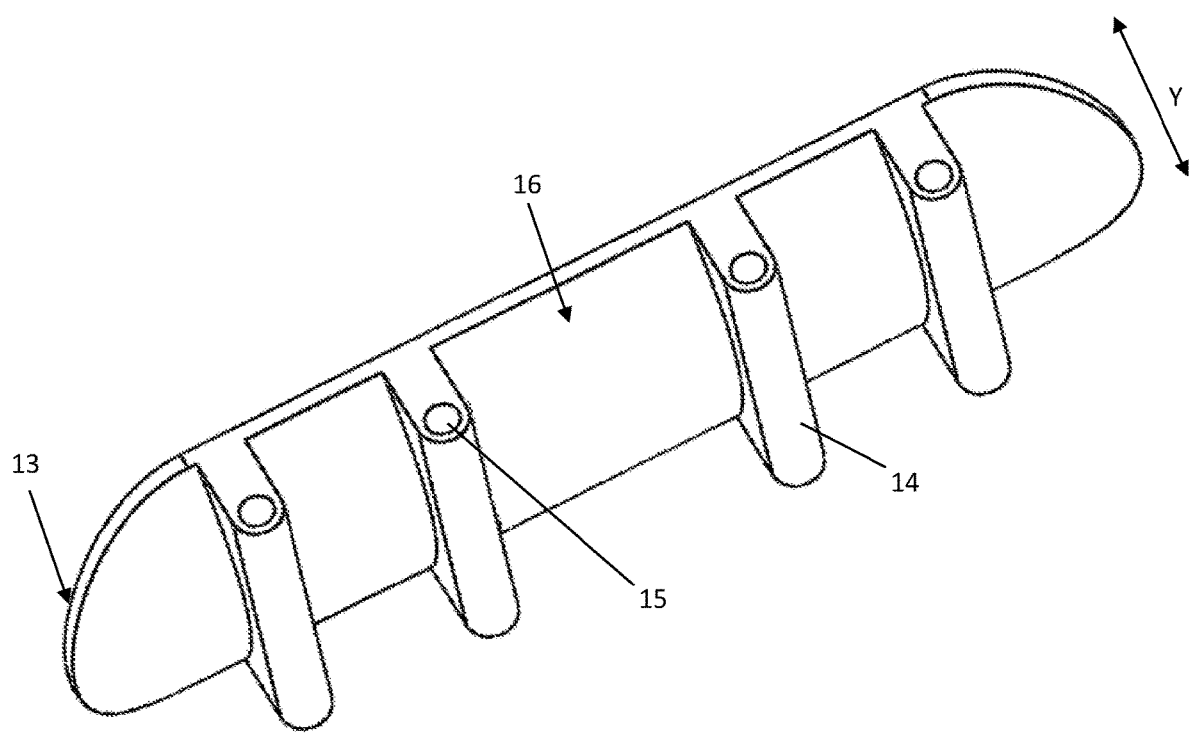
FIG. 2 shows a perspective view of the shield as shown in FIG. 1.

Referring to FIGS. 1 and 2 of the drawings, a blood vessel shield 10 in accordance with the present invention may be formed from any suitable biocompatible, flexible material. The flexible material may have plastic or elastic deformation properties, allowing shields to be formed either in a fixed, but flexible moulded form using a flexible material with elastic properties, or formed from a flexible material with plastic deformation properties. This latter option would provide for the formation of a shield that may be bent into a desired position as required either prior to or during surgery.

The formation of a shield from a material with plastic deformation allows a surgeon to alter the shield shape in response to any abnormalities or anatomical obstacles that may be discovered during surgery. The ability to alter the shape of the shield provides further options for allowing the shield to be used in multiple locations at different stages of a surgery if required, or when the shield is moved to protect other veins as the surgery progresses.

The shield material should be smooth-surfaced at least on a first side to prevent any unnecessary damage to the surrounding tissue. Blood vessels and veins in particular are very fragile and smooth surfaces are required to ensure the walls of the vein are not compromised during the relocation of the vein.

Example of materials that may be used in the formation of the surgical shield are acrylonitrile butadiene styrene (ABS) or polypropylene, silicon or other medical grade plastic material.

In potential embodiments of the invention the one or more walls of the present invention may include a structure to help support the curvature of the shield. For example a thin wire or wire lattice may be incorporated into the walls of the shield, enabling the shield to be bent or curved into various positions as required by the user.

In one preferred embodiment shown in FIGS. 1 and 2, shield 10 is substantially straight along length X and curved across width Y. The shield 10 is a strip or wall 16 of flexible, deformable material with a length of approximately 75 mm-100 mm, although this size is not intended to be limiting.

In use, the shield 10 may be used as a straight shield, or may be curved along width X in either a convex or concave manner by the user as required for a specific surgical use. In some uses, shield 10 may be deformed to introduce two or more curves to the shield, as may be required when placing the shield in various locations throughout the body. This may be to enable optimal placement of pins through apertures 15 located within ribs 14 into a suitable bone structure, or to avoid or protect a specific anatomical area or particular soft tissue.

In this embodiment, shield 10 may be formed using a material with plastic deformation properties, in order for the shield to retain the desired shape once moulded or bent into position. Alternatively, shield 10 may incorporate a thin wire or wire lattice within the plastic structure (not shown). In this embodiment it is preferred that any internal structures used to maintain the shield shape, such as wires, are enclosed within the plastic of the shield to prevent any sharp edges or points from reaching the shield surface. Such sharp protrusions may damage blood vessels or other soft tissue in the area.

In preferred embodiments, the strip or wall 16 is approximately 10 to 15 mm wide (Y), and is bent into a smooth curve across width Y, so as to provide a concave curve 13 along the whole length of the strip, on the convex surface 11, as shown in FIG. 2. This allows for a blood vessel or similar to rest within the curve of the shield produced by a curve in direction Y. This is not however intended to be limiting, and it is also envisaged that the shield may be formed substantially straight along width Y as well as length X, again allowing the user to curve or bend the shield as required for a particular operation.

In circumstances where it is not necessary to move a blood vessel, but a shield is beneficial to decrease risk of damage, shield 10 may be used in a substantially planar or straight configuration, as a curved lip would not be required.

The length of the strip and the width of the strip may be variable. The length needs to be sufficient to permit bending the strip into a smooth gradual curve, but, the length and width may be varied to suit particular applications.

In further embodiments, two or more shields may be connected together to form a longer shield. Shields may be connected by a range of connection means such as a friction fit mechanism, clip-fit mechanism, lock and key mechanism, hook or rim. Shields may also be connected using a shared pin or screw by overlapping a pin or screw receiving means from each of the shields and securing with a single pin or screw.

The shield 10 is formed with four spaced ribs 14, arranged as two pairs of ribs, one pair on each arm 10a, 10b, of the shield 10. Each of the ribs 14 extends substantially the full width of the shield 10 and is formed with an aperture 15 along its length. Each aperture 15 is dimensioned to receive a securing pin or small screw, so that the shield 10 can be secured in place by passing securing pins or screws through each of the apertures 15 and into underlying bone.

Each pin-receiving means may consist of any suitable means for engaging with a securing pin e.g. a flap of material through which a pin may be pushed or a series of eyelets or an apertured rib.

In other embodiments not shown, the shield may include a variety of other attachments means adapted to enable attachment of the shield to an underlying bone. For example the shield 10 may include apertures formed directly within the wall of the shield for receiving pins or screws, or may include pins over-moulded within the shield providing a single piece shield for attachment to the body. Clips or hooks may be directly or indirectly attached to the shield to provide alternative forms of attachment.

The shield of the present invention may be used as follows in the example of shielding the iliac vein when using the shield of FIGS. 1 and 2: During surgery, the blood vessel which needs to be temporarily repositioned to allow good surgical access is exposed. Shield 10 is bent along length X by applying pressure to the ends of the shield 20 in direction Z to bend shield from a substantially straight length X to a curved length X, creating a surface 11 that has a convex form that may be then brought into contact with the blood vessel, such that the blood vessel lies in the concave curve 13 on the convex surface 11 of the shield. Pressure in direction Z is applied until a suitable curved is created that fits the patient's anatomy. The shield is then gently moved to reposition the blood vessel clear of the area where surgery is to be performed, and is secured in position by inserting pins through the apertures 15 and into underlying bone. If necessary the shield may be bent or curved slightly at other points in order to ensure optimal fixation of pins into the underlying bone structure.

The shape of the concave curve 13 assists in retaining the blood vessel in position on the convex surface 11 of the shield, without slipping off. 5 The gentle curvature of the shield through an obtuse angle repositions the blood vessel gradually and smoothly, without any undue pressure on any part of the vessel or any risk of kinking. A further advantage is that, when correctly positioned, the shield 10 lies between the blood vessel and any surgery which is being performed, so that it offers protection to the blood vessel from any surgical accidents such as a scalpel slipping during the operation.

In other embodiments not shown, the shield wall may be essentially planar in width Y, with the exception of a curved lip located along the length X, or a portion of the length X, of the lower edge. This embodiment also allows a blood vessel to lie within the curved lip to aid in repositioning of the vessel without risk of damage. As would be clear to a person skilled in the art, the size and shape of the curve or lip on the shield may be adapted to the size and type of soft tissue being protected.

In alternative embodiments of the invention, an alternative shield that may be used for use with an iliac vein can be seen in FIGS. 4 to 7, where shield 10 is curved both along its length X and across its width Y. In preferred embodiments, the shield 10 is formed as a strip of flexible material with a length of approximately 75 mm, which is bent to form a smooth, gradual curve through an obtuse angle A typically of the order of 120°. In this way, the shield 10 provides a first, convex surface 11 and a second, concave, surface 12.

Figure 4:
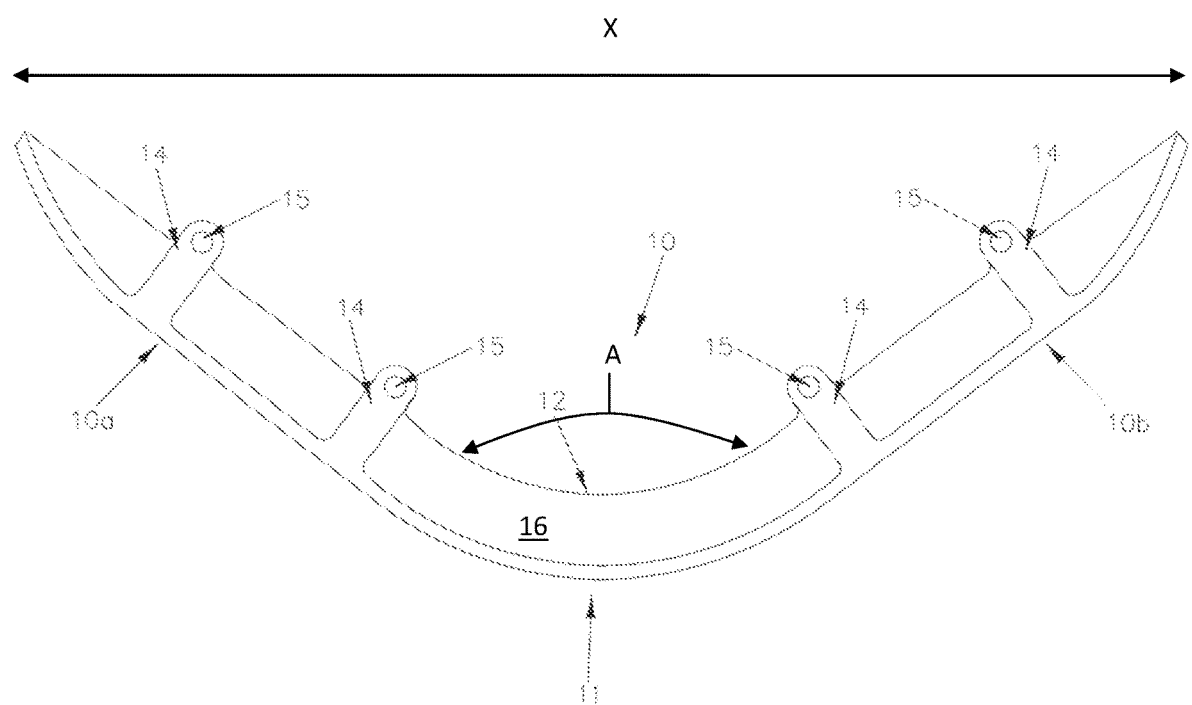
FIG. 4 shows a top view of a surgical shield in accordance with a second embodiment of the invention.
Figure 5:
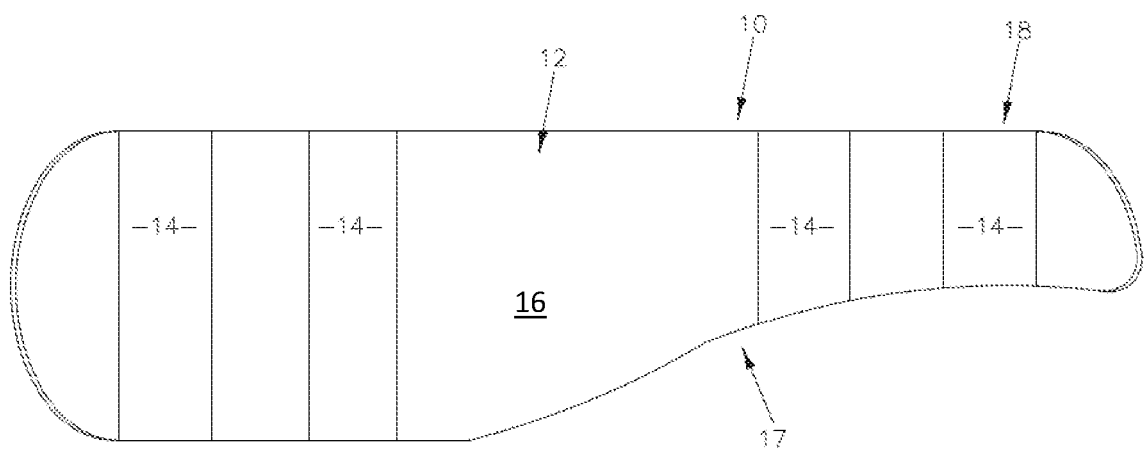
FIG. 5 shows a side view of a surgical shield in accordance with a second embodiment of the invention.
Figure 7:
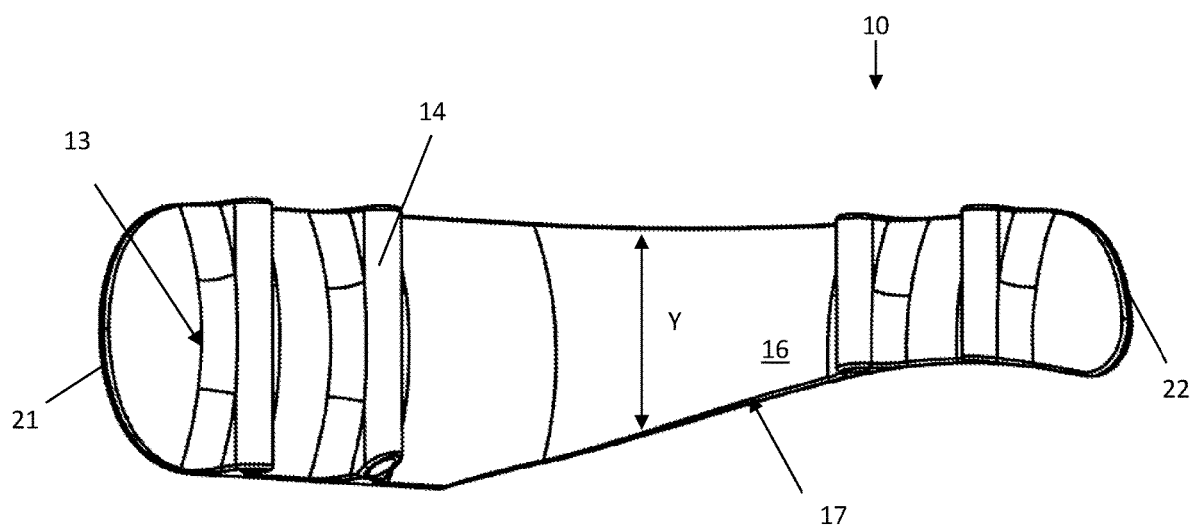
FIG. 7 shows a side perspective view of a surgical of FIGS. 4-6.

The strip is approximately 10 to 15 mm wide, and is bent into a smooth curve across its width Y, so as to provide a concave curve 13 along the whole length of the strip, on the convex surface 11, as shown in FIGS. 4 and 7.

The angle through which the shield is curved along its length should be an obtuse angle, i.e. the curve should be a smooth gradual curve and sharp angles should be avoided, however this angle does not need to be precisely 120°. The shield need not be symmetrical i.e. it can be longer on one side of the obtuse angle than on the other. The final design and placement of the angle may be determined prior to manufacture, for producing a large quantity of shields for a common purpose, or may be decided following manufacture, using a deformable shield that can be curved or bent in situ.

On the concave surface 12, the shield 10 is formed with four spaced ribs 14, arranged as two pairs of ribs, one pair on each arm 10a, 10b, of the shield 10. Each of the ribs 14 extends substantially the full width of the shield 10 and is formed with an aperture 15 along its length. Each aperture 15 is dimensioned to receive a securing pin, so that the shield 10 can be secured in place by passing securing pins through each of the 30 apertures 15 and into underlying bone.

The shape of the concave curve 13 assists in retaining the blood vessel in position on the convex surface 11 of the shield, without slipping off. 5 The gentle curvature of the shield through an obtuse angle repositions the blood vessel gradually and smoothly, without any undue pressure on any part of the vessel or any risk of kinking. A further advantage is that when correctly positioned, the shield 10 lies between the blood vessel and any surgery which is being performed, so that it offers protection to the 10 blood vessel from any surgical accidents such as a scalpel slipping during the operation.

When the operation is completed, the pins are withdrawn from the apertures 15 and the shield 10 is removed and discarded.

A further variant on the surgical shield is described with reference to FIGS. 14 to 7. This shield is the substantially same as the shield shown in FIGS. 1 and 2 except as described below, and the same reference numerals are used for similar parts. These same variations may be applied to any shield with a range of curves or planar surfaces.

Figure 3:
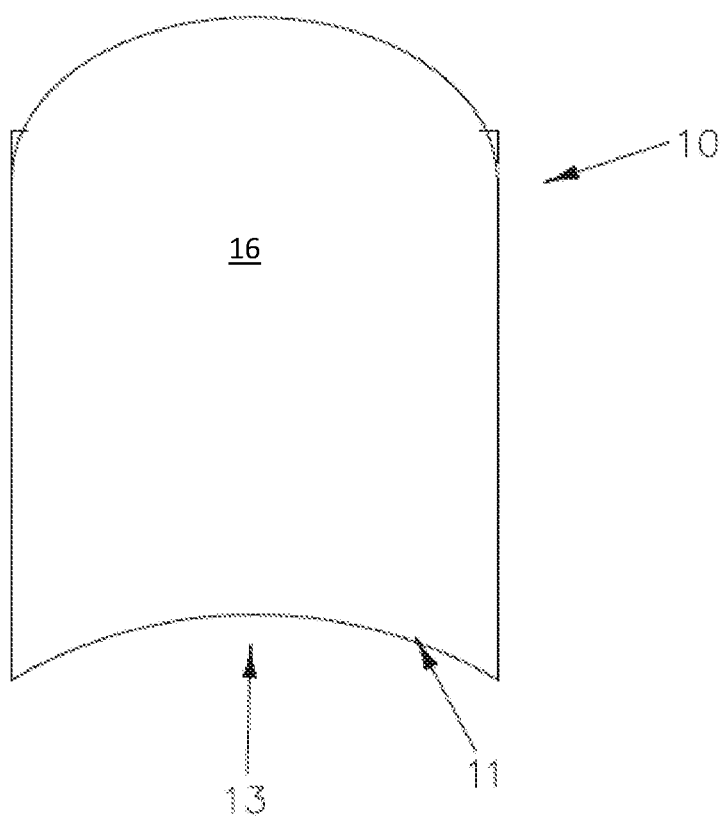
FIG. 3 shows an end view of the shield of FIGS. 1 and 2.
Figure 6:
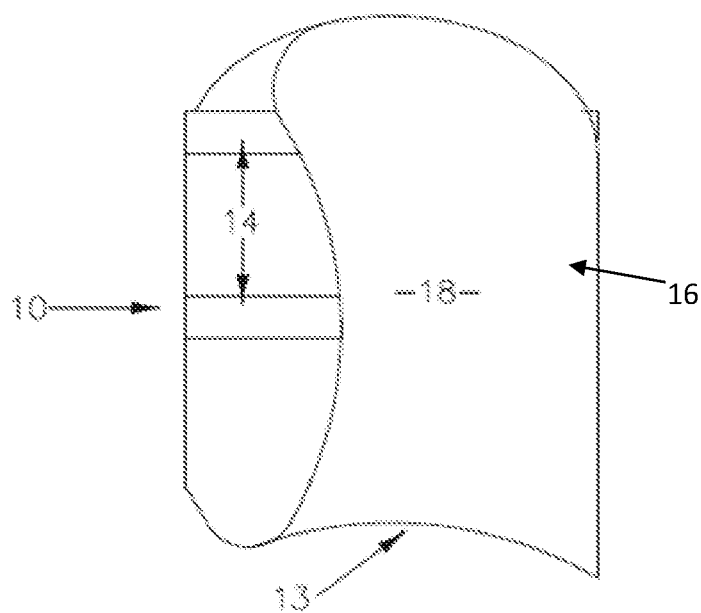
FIG. 6 shows an end view of the shield of FIGS. 4 and 5.

In FIGS. 3, 6 and 7 a portion of edge 17 of shield 10 is cut away to give a shield of variable width across the length of the shield, with a narrower portion 18 at end 22. The ribs 14 on the narrower portion 18 are shortened as necessary.

Preferably the cutaway portion of shield 10 provides a shield with a first end 21 approximately twice the width of second end 22.

The provision of the cutaway portion permits the lower edge of the shield in use to conform to the shape of the underlying vertebrae. This enables the shield to rest more securely in position when secured to the vertebra. In other embodiments the shield may be cut away in different areas to more effectively be positioned in any part of the body where there may be anatomical obstacles. The edges of the elongate member may include notches, curves or tapers or other irregularities in edge shape as needed to conform to different anatomical regions where the shield may be located.

The shield of the present invention may include a number of further features not shown in the Figures. The shield may be a bendable double sided shield, with a smooth surface provided on each side of the shield. In the case of a double sided shield, attachment means may be located within the walls of the shield, for example in the form of apertures running the width of the shield for receiving pins or screws.

The shields of the present invention may be formed using a variety of techniques, for example injection moulding, additive manufacturing or plastic machining techniques.

The surgical shield of the present invention provides a number of advantages to both surgeons and patients. By careful shielding of blood vessels, nerves or other tissues within the body, the likelihood of damage is significantly reduced. Damage to veins or arteries can result in significant blood loss for a patient, and nerve damage may be irreversible. The shield, when strategically positioned between a vulnerable area and the surgeon's working location, can prevent injury caused by a slip of a scalpel or other sharp instrument.

When used in the repositioning of blood vessels, the curvature of the shield provides a smooth support for the vessel to rest in when being moved. This is a significant improvement on known techniques of moving the blood vessel with a pin, fingers, or surgical tool, which can increase blood pressure by pinching of the vessel and risk damage to the vessel wall.

Such a shield is envisaged to be used in a wide range of locations within the body and may be formed as a flexible, versatile tool for a wide range of surgical applications.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

We claim:

1. A surgical shield for temporarily repositioning a blood vessel and/or protecting a body part such as a blood vessel, lymphatic vessel, nerve or ureter during surgery, wherein the shield includes;
    a one or more wall including at least one substantially smooth surface, the one or more wall forming a single substantially elongate member and providing along the length of the elongate member a smooth, gradual curve through an obtuse angle, such that the elongate member includes a first surface providing a convex curve, said convexly curved surface of said shield also providing a concave curve across a width of the elongate member; and
    wherein the shield includes two or more ribs, the ribs extending across the width of the shield or part thereof and formed with an aperture therein adapted to receive a pin, such that in use, the pin is capable of extending through the aperture in the rib and fixing to a body portion below, retaining the shield in a substantially upright position resting on an elongate edge of the shield wall
    at least one attachment means selected from the group of an aperture, groove, pin, screw, hook, nail or clip directly or indirectly attached to the one or more walls for securing the shield in position during a surgery.

2. The shield of claim 1, wherein the shield includes one or more curvature supports.

3. The shield of claim 2 wherein the one or more curvature supports are in the form of one or more wires or wire lattices located within the one or more wall.

4. The surgical shield of claim 1, wherein the shield includes four spaced apart ribs.

5. The surgical shield of claim 4 wherein the ribs are located on the first surface of the elongate member within the obtuse angle of the shield.

6. The surgical shield of claim 1, wherein the one or more walls is a single elongate strip of flexible material.

7. The surgical shield of claim 1, wherein the first surface providing a convex curve is substantially smooth.

8. The surgical shield of claim 1, wherein the obtuse angle is approximately 120°.

9. The shield of claim 1, wherein the surgical shield includes a taper along the length of one or both side edges of the elongate member whereby a first end of the elongate member has a greater width than a second end of the elongate member.

10. The shield of claim 1, wherein one or both of the side edges of the elongate member includes a notch, cut out portion or irregular edge to correspond to a specific anatomical region.

11. The shield of claim 1, wherein the attachment means comprises an aperture adapted to receive a pin.

12. The shield of claim 1, wherein the shield and attachment means are integrally formed.

13. The shield of claim 1, wherein the surgical shield includes at least one connection mechanism for releasably connecting the surgical shield to a second surgical shield.

14. The surgical shield of claim 1, wherein the elongate member includes a curved lip located along the lower elongate edge or a portion thereof of the elongate member.

15. A surgical shield for temporarily repositioning a blood vessel and/or protecting a body part such as a blood vessel, lymphatic vessel, nerve or ureter during surgery, wherein the shield includes;
    a one or more wall including at least one substantially smooth surface, the one or more wall forming a single substantially planar elongate member, the elongate member including a curved lip located along the lower elongate edge or a portion thereof of the elongate member; and
    wherein the shield includes two or more ribs, the ribs extending across the width of the shield or part thereof and formed with an aperture therein adapted to receive a pin, such that in use, the pin is capable of extending through the aperture in the rib and fixing to a body portion below, retaining the shield in a substantially upright position resting on an elongate edge of the shield wall
    at least one attachment means selected from the group of an aperture, groove, pin, screw, hook, nail or clip directly or indirectly attached to the one or more walls for securing the shield in position during a surgery.

16. The shield of claim 15, wherein the shield includes one or more curvature supports.

17. The shield of claim 16 wherein the one or more curvature supports are in the form of one or more wires or wire lattices located within the one or more wall.

18. The surgical shield of claim 15, wherein the shield includes four spaced apart ribs.

19. The surgical shield of claim 18 wherein the ribs are located on one side of the elongate member.

20. The surgical shield of claim 15, wherein the one or more wall is a single elongate strip of flexible material.

21. The shield of claim 15, wherein the surgical shield includes a taper along the length of one or both side edges of the elongate member whereby a first end of the elongate member has a greater width than a second end of the elongate member.

22. The shield of claim 15, wherein one or both of the side edges of the elongate member includes a notch, cut out portion or irregular edge to correspond to a specific anatomical region.

23. The shield of claim 15, wherein the attachment means includes an aperture adapted to receive a pin.

24. The shield of claim 15, wherein the surgical shield includes at least one connection mechanism for releasably connecting the surgical shield to a second surgical shield.

* * * * *